(12) United States Patent
Gillespie, III

(10) Patent No.: US 11,583,473 B2
(45) Date of Patent: Feb. 21, 2023

(54) INTEGRATED INJECTABLE DRUG PACKAGING AND DELIVERY SYSTEM AND METHODS OF USE

(71) Applicant: Nspire Medical Technologies, LLC, Athens, TX (US)

(72) Inventor: Richard David Gillespie, III, Athens, TX (US)

(73) Assignee: Nspire Medical Technologies, LLC, Athens, TX (US)

( * ) Notice: Subject to any disclaimer, the term of this patent is extended or adjusted under 35 U.S.C. 154(b) by 0 days.

(21) Appl. No.: 17/487,647

(22) Filed: Sep. 28, 2021

(65) Prior Publication Data

US 2022/0096329 A1  Mar. 31, 2022

Related U.S. Application Data

(60) Provisional application No. 63/085,298, filed on Sep. 30, 2020.

(51) Int. Cl.
*A61M 5/00* (2006.01)
*A61J 1/20* (2006.01)

(52) U.S. Cl.
CPC ............. *A61J 1/2096* (2013.01); *A61J 1/201* (2015.05); *A61J 1/2027* (2015.05); *A61J 1/2048* (2015.05)

(58) Field of Classification Search
CPC .. A61M 5/284; A61M 5/285; A61M 5/31596; A61M 5/3294; A61M 3/005; A61M 5/2066; A61J 1/2003; A61J 1/2048; A61J 1/2027; A61J 1/201; A61J 1/2096
See application file for complete search history.

(56) References Cited

U.S. PATENT DOCUMENTS

| | | | |
|---|---|---|---|
| 3,756,390 A | 9/1973 | Abbey et al. | |
| 4,254,768 A | 3/1981 | Ty | |
| 4,331,146 A | 5/1982 | Brignola | |
| 5,876,372 A * | 3/1999 | Grabenkort | A61M 5/31596 604/89 |
| 6,387,078 B1 | 5/2002 | Gillespie, III | |
| 6,692,468 B1 | 2/2004 | Waldenburg | |
| 6,817,987 B2 | 11/2004 | Vetter et al. | |
| 6,846,300 B2 | 1/2005 | Hörth et al. | |
| 6,902,543 B1 | 6/2005 | Cherif-Cheikh et al. | |
| 7,959,600 B2 | 6/2011 | Chang et al. | |
| 9,174,002 B2 | 11/2015 | Chang et al. | |
| 10,105,285 B2 | 10/2018 | Chang | |
| 2003/0012690 A1 | 1/2003 | Taylor et al. | |
| 2006/0142701 A1 | 6/2006 | Thorne | |
| 2015/0141913 A1 | 5/2015 | Bartlett et al. | |
| 2018/0344933 A1 * | 12/2018 | Dittrich | A61M 5/31596 |
| 2019/0282759 A1 * | 9/2019 | Orofino | A61M 5/285 |

* cited by examiner

*Primary Examiner* — Rebecca E Eisenberg
(74) *Attorney, Agent, or Firm* — Stephen Y. Liu; Carstens, Allen & Gourley, LLP

(57) ABSTRACT

An injection apparatus and related methods. The injection apparatus includes a housing with a proximate end and a distal end. The housing further defines a fluid pathway. A defeatable seal is fixedly positioned within the fluid pathway to separate an internal volume of the housing into a first compartment and a second compartment downstream from the first compartment. The defeatable seal is configured to fail in response to an increase in fluid pressure within the first compartment, allowing a fluid in the first compartment to pass through the second compartment and through the fluid outlet.

19 Claims, 16 Drawing Sheets

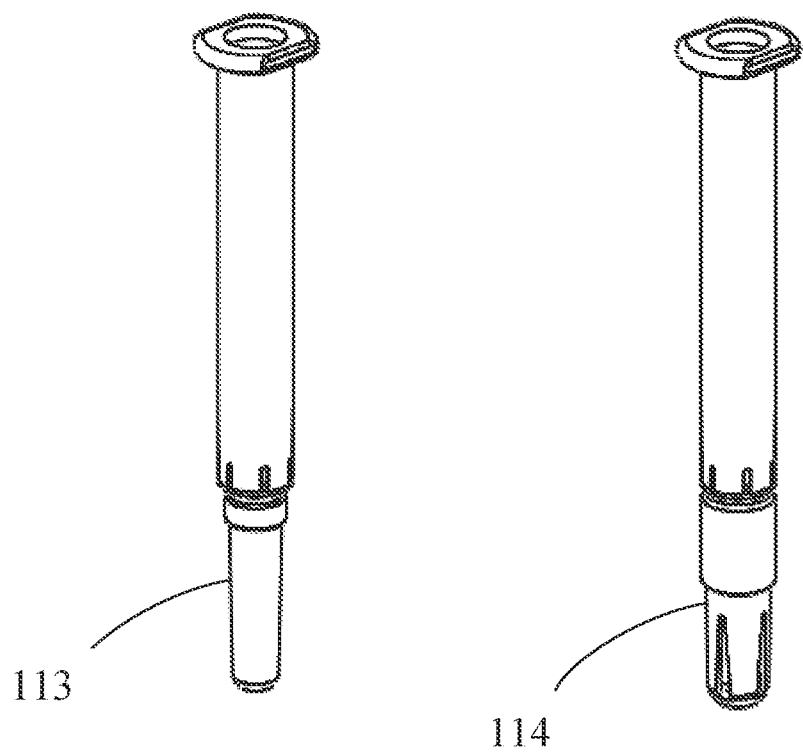

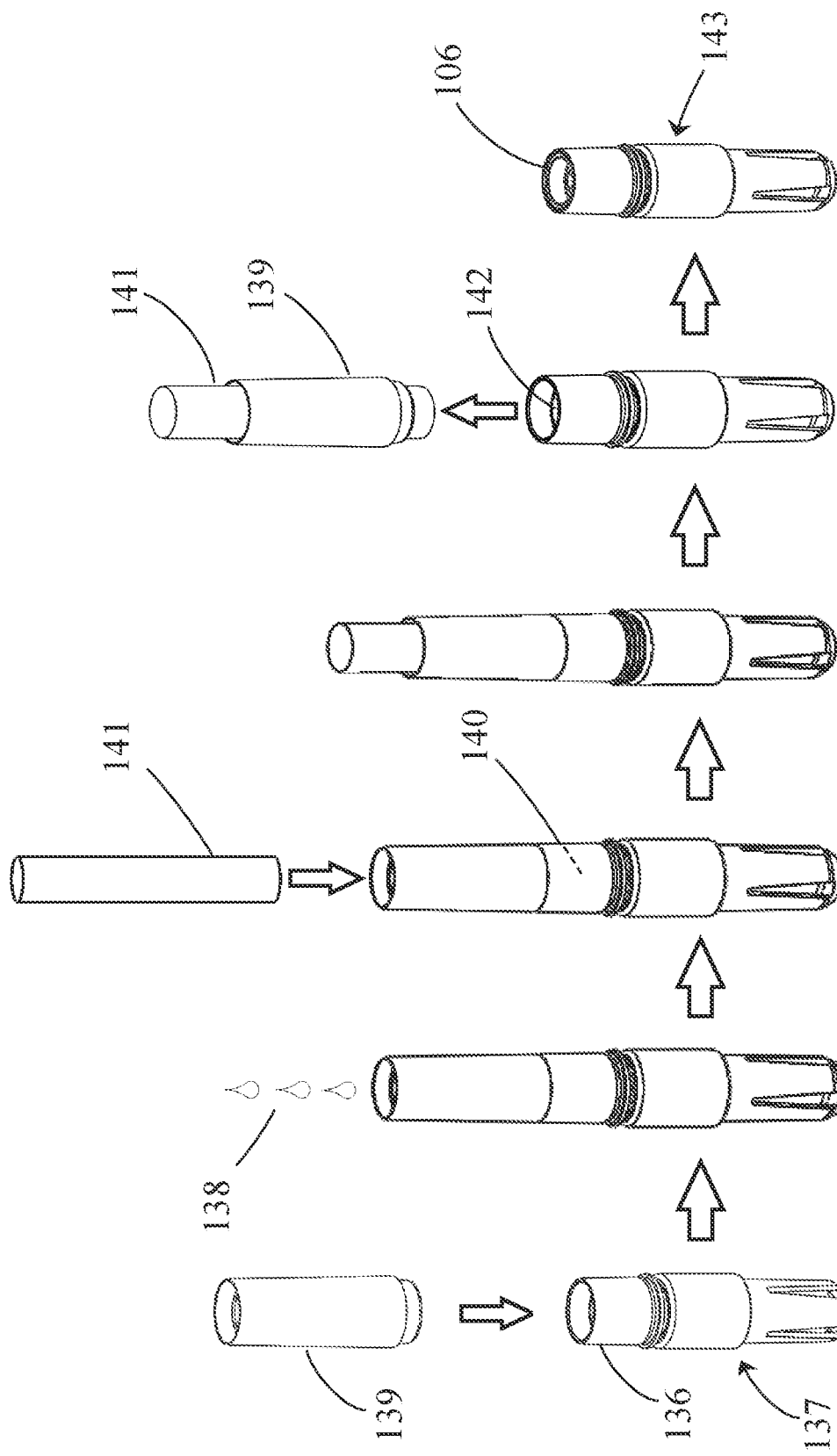

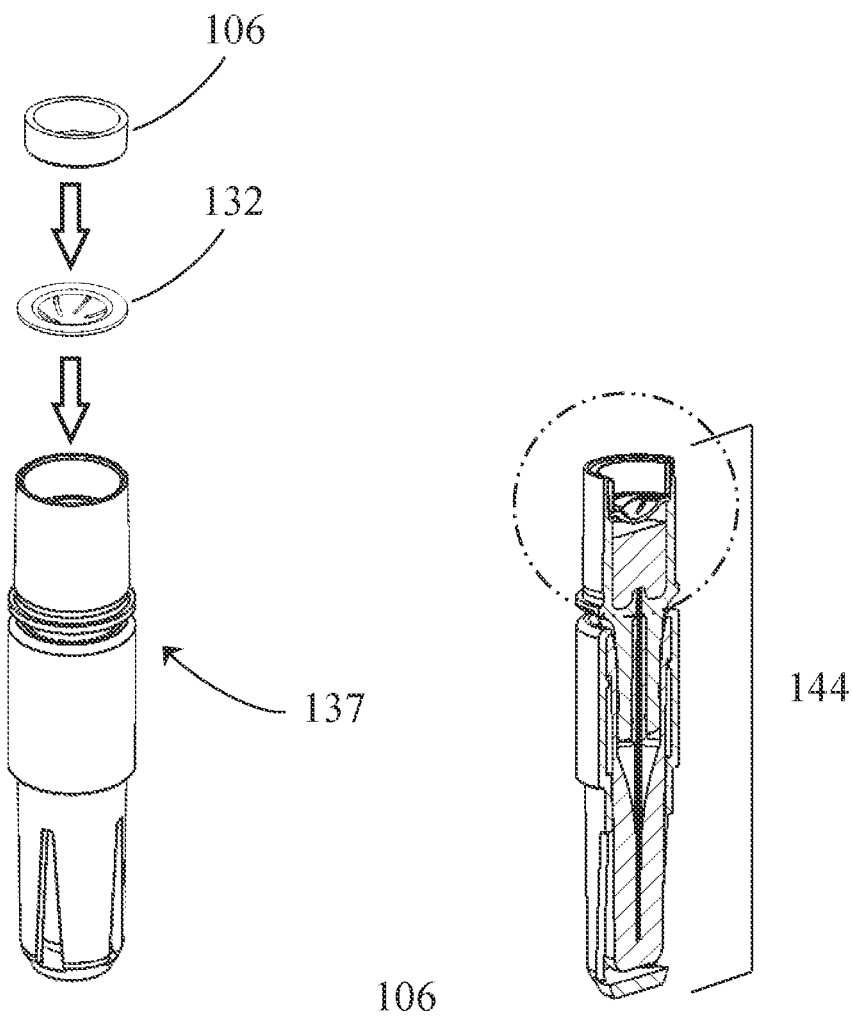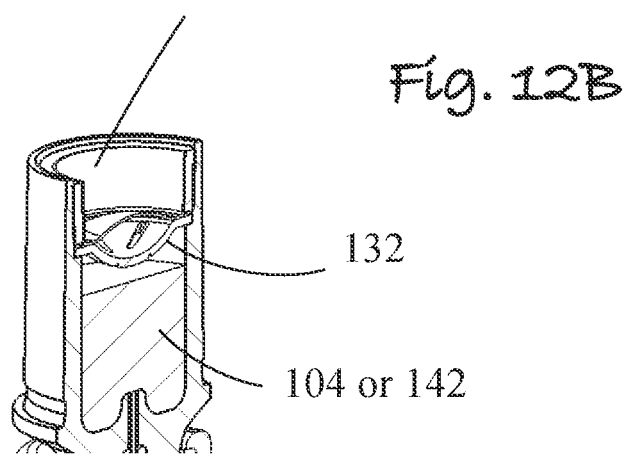

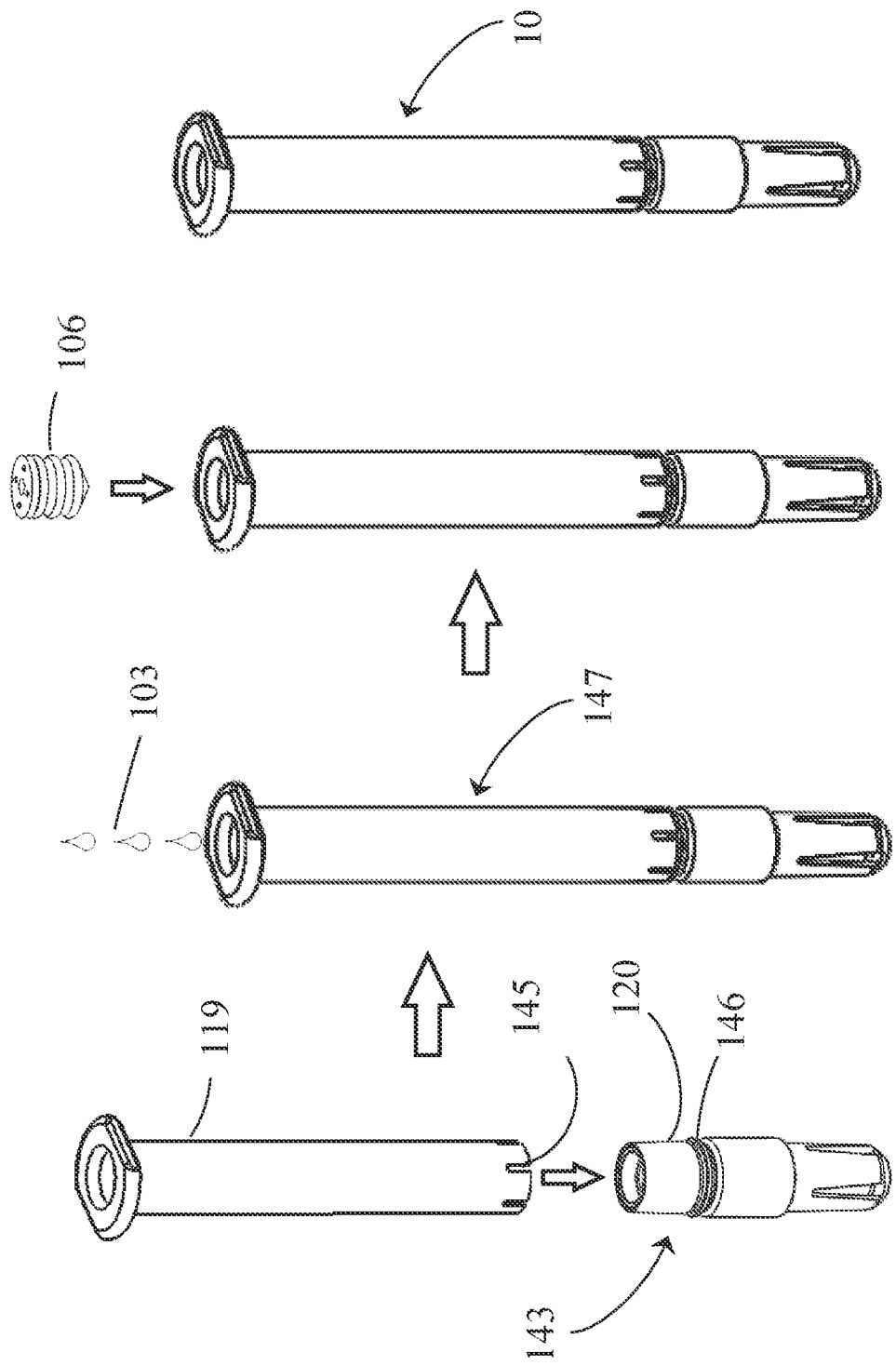

INTEGRATED INJECTABLE DRUG PACKAGING AND DELIVERY SYSTEM AND METHODS OF USE

BACKGROUND

Technical Field

Novel aspects of the present disclosure relate to the field of injectable drug therapeutics and more particularly, to an integrated drug package and delivery system for a lyophilized therapeutic substance and a liquid diluent.

Background

Many injectable therapeutic substances, e.g., vaccines and biopharmaceutical compounds, are often lyophilized to extend their usable shelf life and forego the need for refrigeration. Lyophilized compounds are typically packaged in vials which afford robust protection from ingress of water vapor, oxygen, and pathogens. However, lyophilized compounds packaged in vials require a liquid diluent, e.g., sterile water for injection or sterile saline, packaged separately, to be introduced into the vial in order to reconstitute the lyophilized drug into a liquid form appropriate for parenteral injection. Often the diluent is packaged in a pre-filled syringe which allows the user to introduce the diluent into the vial by first penetrating the vial septum with the hypodermic needle constituent of the syringe. Upon penetrating the vial septum, the diluent is conveyed from the syringe into the vial. The drug is then reconstituted and a portion of the reconstituted drug is aspirated back into the syringe. The syringe is then withdrawn from the vial and used to inject the reconstituted drug product into the recipient of the injection. Thus, one current state-of-the-art drug packaging comprises two independent packages, one for the lyophilized compound and one for the diluent. Preparing the drug for injection requires multiple user steps.

Importantly, it is not possible for all of the reconstituted drug within a vial to be harvested; some of the drug product always remains within the vial after aspiration. This well-known fact necessitates overfilling the vial with drug product in anticipation of loss and results in an inherent waste of the valuable drug. In addition to the foregoing, there is a growing trend to afford patients that must receive injections as part of a medical therapy the means to self-medicate. Automatic self-injection devices such as auto-injectors have become increasingly popular and commonplace. They are widely recognized as a valuable means to enable medically untrained users to self-administer injections while avoiding the emotional trauma often associated with the use of conventional syringes. It has been proven that providing injectable substances in self-injection devices increases patient compliance with their prescribed therapy and thereby improves medical outcomes. Packaging a lyophilized drug in a vial that necessitates a separate reconstitution step does not easily lend itself to self-injection devices.

In order to accommodate this self-administration trend, pharmaceutical companies often formulate their injectable drugs into a liquid-stable form that can be packaged in pre-filled syringes. A pre-filled syringe containing the injectable drug minimizes the primary packaging requirement, reduces the need for overfill and waste of drug product, provides superior ease-of-use, and easily integrates into a self-administration mechanism. However, the liquid-stable drug formulation process carries with it a vast array of challenges and program risks and necessitates a lengthy process of proving stability of the liquid drug within the pre-filled syringe. For new, proprietary drugs this process can consume a considerable fraction of the time the drug benefits from patent protection. Moreover, liquid-stable drugs, e.g. therapeutic proteins, often require refrigeration from the time they are produced until they are used. This requirement for continuous refrigeration from manufacturer to user, referred to by those skilled in the art as "cold chain", adds considerable cost to the drug, both in terms of secondary packaging and logistics. In summary, lyophilized drugs provide the benefits of superior stability and shorter commercialization timelines, among other benefits, but inferior ease-of-use; liquid-stable drugs packaged in pre-filled syringes provide superior ease-of-use but require a longer timeframe to commercialize, achieve inferior stability, necessitate refrigeration, and are beset with other limitations.

Thus, for the reasons cited above, among others, there remains a present and increasing need for a packaging and delivery system that would incorporate the advantages of lyophilized drugs and the ease-of-use of liquid-stable drugs packaged in pre-filled syringes.

SUMMARY OF THE INVENTION

Novel aspects of the present disclosure are directed to an injectable drug packaging and delivery system and method in which a lyophilized medicinal substance is brought into solution with a liquid diluent and concurrently injected into living tissue upon actuation by the user. The present disclosure thereby combines the advantages of storing a drug substance a lyophilized state and the ease-of-use of a pre-filled syringe.

In a first embodiment, the injection apparatus includes a housing with a proximal end and a distal end. The housing further defines a fluid pathway. A defeatable seal is fixedly positioned within the fluid pathway to separate an internal volume of the housing into a first compartment and a second compartment downstream from the first compartment. A fluid outlet is disposed at the distal end of the housing. The defeatable seal is configured to fail in response to an increase in fluid pressure within the first compartment, causing a fluid in the first compartment to pass through the second compartment and through the fluid outlet.

In a second embodiment, the injection apparatus includes a housing with a proximate end and a distal end. The housing further defines a fluid pathway. A defeatable seal is fixedly positioned within the fluid pathway to separate an internal volume of the housing into a first compartment and a second compartment downstream from the first compartment. A piston is slidably engaged within the first compartment and a hypodermic needle is disposed at the distal end of the injection apparatus, coupled to a fluid outlet. A diluent is sealed within the first compartment between the piston and the defeatable seal, and a lyophilized substance is sealed within the second compartment. The defeatable seal is configured to fail in response to an increase in fluid pressure within the first compartment caused by a compressive force imparted to the piston, causing the diluent in the first compartment flow past the defeated seal to mix with the lyophilized substance in the second compartment to form an injectate expelled from the hypodermic needle.

In a third embodiment, a method of manufacturing an injection apparatus is disclosed. The method includes the steps of dispensing a unit dose of a lyophilizate substance into an opening of a lyophilizate compartment subassembly; installing a defeatable seal onto the opening of the lyophilizate compartment subassembly thereby sealing the compartment; securing a liquid containment member to the lyophilizate compartment subassembly; dispensing a diluent into the liquid containment member; and sealing the liquid containment member with a slidable piston.

Other aspects, embodiments and features of the novel aspects of this disclosure will become apparent from the following detailed description when considered in conjunction with the accompanying figures. In the figures, each identical, or substantially similar component that is illustrated in various figures is represented by a single numeral or notation. For purposes of clarity, not every component is labeled in every figure. Nor is every component of each embodiment of this disclosure shown where illustration is not necessary to allow those of ordinary skill in the art to understand the novel aspects disclosed herein.

BRIEF DESCRIPTION OF THE FIGURES

The novel features believed characteristic of the invention are set forth in the appended claims. The invention itself, however, as well as a preferred mode of use, further objectives and advantages thereof, will be best understood by reference to the following detailed description of illustrative embodiments when read in conjunction with the accompanying figures, wherein:

FIGS. 7A-7B illustrate two exemplary embodiments of the present disclosure shown with and without a needle shield jacket;

FIGS. 11A-11F illustrate another series of schematic diagrams depicting alternative production steps of an integrated injectable drug packaging and delivery system subassembly containing the lyophilized therapeutic substance;

FIGS. 12A-12C illustrate assembly details of an exemplary embodiment of the present disclosure and associated method in which a flow baffle and housing feature is illustrated and method of assembly described;

FIGS. 13A-13D illustrate a series of schematic diagrams depicting the production of a finished integrated injectable drug packaging and delivery system containing the lyophilized therapeutic substance and diluent in accordance with the present disclosure;

DETAILED DESCRIPTION

Figure 1:
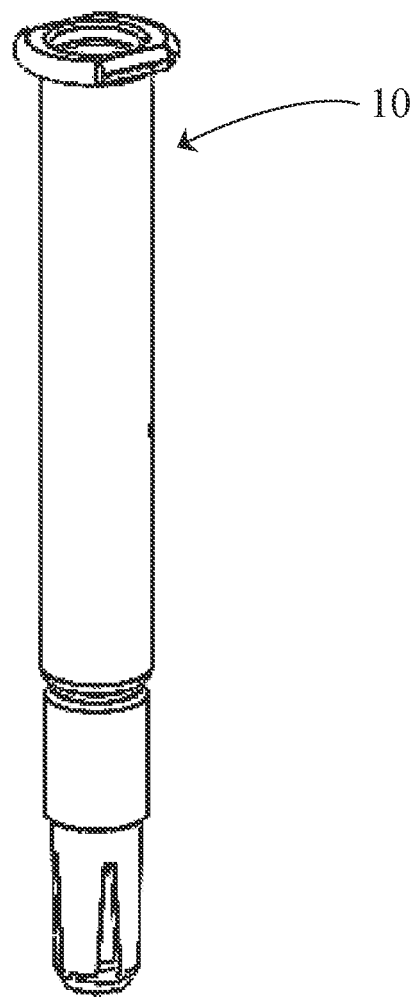
FIG. 1 is an exterior front elevation view of an exemplary embodiment of an integrated injectable drug packaging and delivery system according to the present disclosure.

Novel aspects of this disclosure obviate at least some of the foregoing deficiencies and provide at least some of the foregoing benefits by way of an integrated, injectable drug packaging and delivery system comprising a housing, a first compartment and a second compartment both integral to the housing; a liquid diluent residing in the first compartment isolated from the ambient environment and a lyophilized medicinal substance residing in the second compartment isolated from the ambient environment; the two compartments are separated by a defeatable seal. Preferred embodiments of the integrated injectable drug packaging and delivery system described herein further comprises a hypodermic needle disposed in fluid communication with the second compartment. A piston is also provided in a sealed and slidable relationship with the housing and sealing the first compartment so that the diluent resides between the piston and the defeatable seal. The integrated injectable drug packaging and delivery system described herein is operable by the application of force upon the piston to cause movement of the piston and thus increase the pressure in the first compartment sufficient to defeat the seal and thereby establish fluid communication between the first compartment and the second compartment. Continued movement of the piston in response to applied force causes the diluent to flow from the first compartment past the defeated seal and into the second compartment. As the diluent flows into the second compartment, it takes the medicinal substance into solution or suspension and the medicinal substance-bearing solution, i.e., the injectate, exits the second compartment via the hypodermic needle. The integrated injectable drug packaging and delivery system described herein may further comprise a removable seal disposed about the hypodermic needle and secured in a sealed and separable relationship with the housing whereby the hypodermic needle is isolated from the ambient environment.

As used in this disclosure, the term "proximal" defines the end of the described embodiments opposite the hypodermic needle; that is, the axial direction opposite that of the needle.

The term "distal" similarly defines the needle end of the described embodiments; that is, the axial direction towards the needle. It should also be noted that the terms "first", "second", "third", "upper", "lower", and the like may be used herein to modify various elements. These modifiers do not imply a spatial, sequential, or hierarchical order to the modified elements unless specifically stated.

The term "lyophilizate" is hereinafter used to describe the lyophilized medicinal substance containing the active pharmaceutical ingredient.

The term "actuation" is hereinafter used to describe the action necessary to trigger the mixing and injection process.

An index of reference numerals used in the figures that follow is provided below.

| Reference | Element |
|---|---|
| 10 | integrated injectable drug packaging and delivery system |
| 100 | housing |
| 101 | first compartment |
| 102 | second compartment |
| 103 | diluent |
| 104 | lyophilizate |
| 105 | piston |
| 106 | defeatable seal |
| 107 | interior surface of housing |
| 108 | diluent-facing side of defeatable seal |
| 109 | lyophilizate-facing side of defeatable seal |
| 110 | sealing surface of defeatable seal |
| 111 | interior sealing surface of housing |
| 112 | hypodermic needle |
| 113 | needle shield |
| 114 | needle shield jacket |
| 115 | enclosing sealing surface of needle shield |
| 116 | exterior periphery of hypodermic needle |
| 117 | interior sealing surface at proximal end of needle shield |
| 118 | exterior sealing surface of housing |
| 119 | diluent containment member |
| 120 | lyophilizate containment member |
| 121 | alternative embodiment of housing |
| 122 | (not used) |
| 123 | (not used) |
| 124 | rupture disk |
| 125 | elastomeric seal |
| 126 | convex surface of rupture disk |
| 127 | concave surface of rupture disk |
| 128 | stress raiser groove |
| 129 | stem |
| 130 | ridged needle shield |
| 131 | flange |
| 132 | baffle |
| 133 | flow director |
| 134 | baffle apertures |
| 135 | lyophilizate compartment subassembly |
| 136 | lyophilizate compartment |
| 137 | shielded lyophilizate compartment subassembly |
| 138 | medicament solution |
| 139 | fill tube |
| 140 | higher volume lyophilizate |
| 141 | tamping tool |
| 142 | compacted lyophilizate |
| 143 | lyophilizate-bearing system sub-assembly |
| 144 | lyophilizate-bearing system sub-assembly with baffle |
| 145 | snap fit features |
| 146 | cooperating groove |
| 147 | system subassembly |

Figures 2A, 2B, 2C:
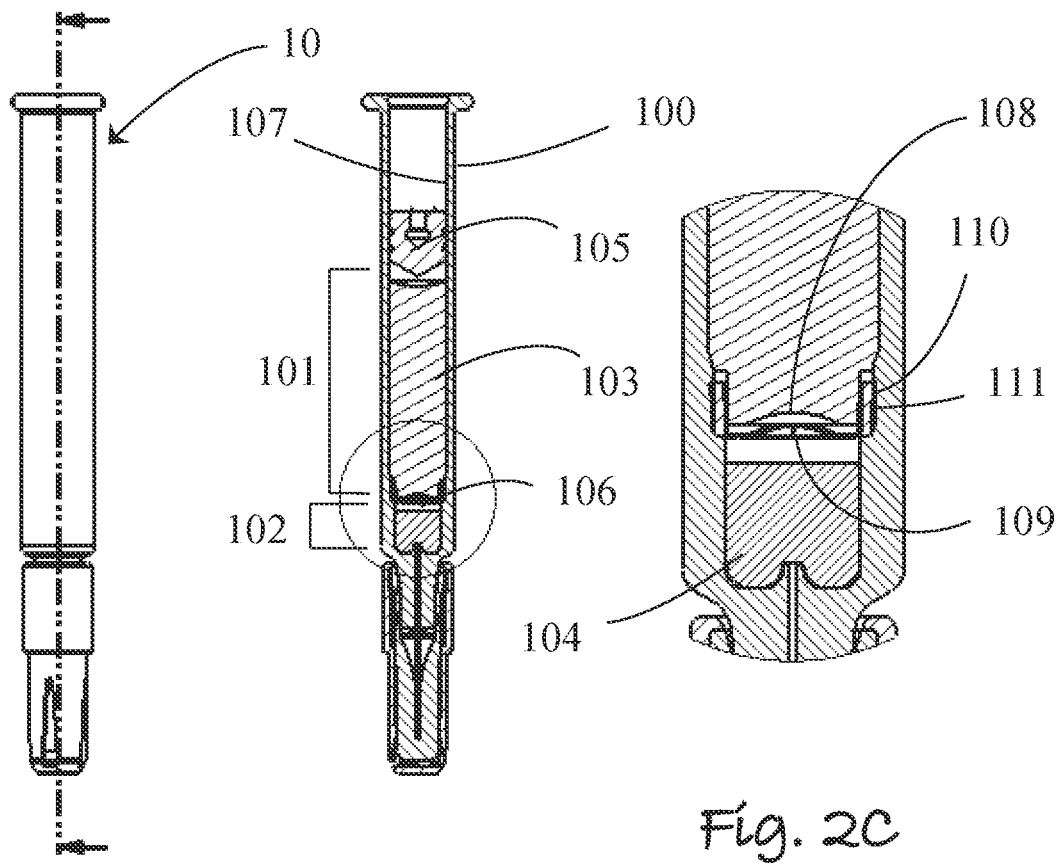
FIGS. 2A-2C are exterior front elevation and sectional views of an exemplary embodiment of an integrated injectable drug packaging and delivery system according to the present disclosure.
Figure 3A:
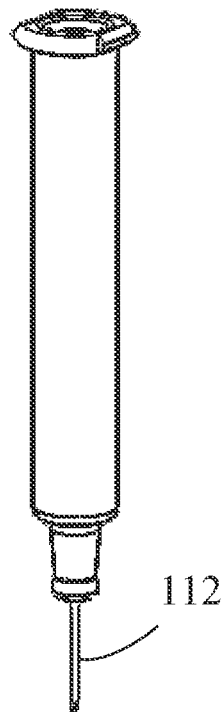
FIGS. 3A-3D illustrate an exemplary embodiment of the present disclosure with different embodiments of needle shields. A sectional detail illustrating needle shield-to-housing engagement is also provided.
Figure 3B:
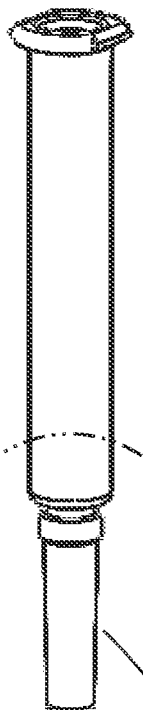
Figure 3C:
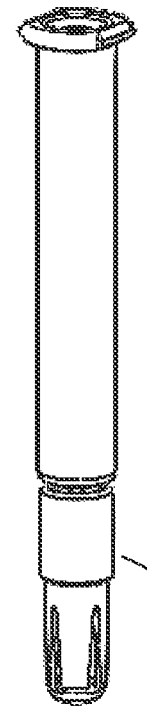
Figure 3D:
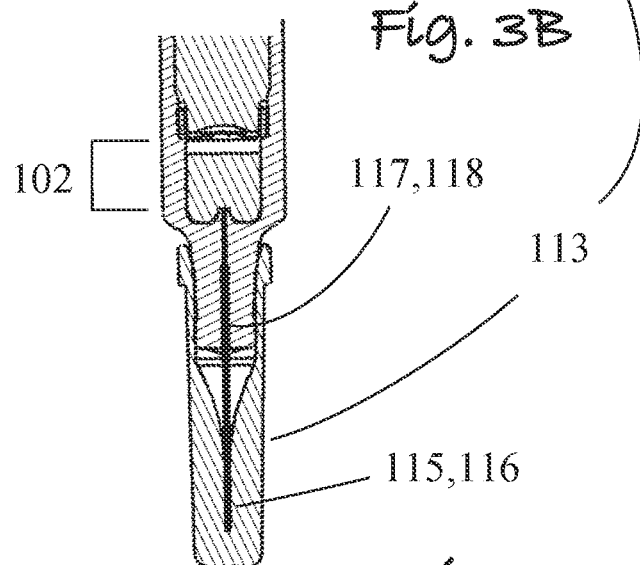

Referring to the figures and particularly to FIGS. 1 and 7, exemplary embodiments of an integrated injectable drug packaging and delivery system 10 (hereinafter the "system") according to the present disclosure are shown. Referring to FIGS. 1 and 2, the exemplary system is generally symmetric about its long axis. The system provides a housing 100 comprising, among other constituents, two compartments; a first compartment 101 and a second compartment 102. The first compartment 101 contains a liquid diluent 103; the second compartment 102 containing a lyophilizate 104. Each compartment is configured to seal the substance stored within them from the ambient environment and from each other. The present disclosure provides a piston 105 constructed of an elastomeric material disposed proximal to the first compartment 101 of the housing 100 and the diluent 103; the piston 105 is configured to cooperate with the interior surface 107 of housing 100 to provide a slide able and sealing relationship with the interior surface 107 of the housing 100 and isolate the diluent from the ambient environment. Referring to FIGS. 2A through 2C, the two compartments 101 and 102 are separated by a defeatable seal 106 disposed within housing 100 with one surface 108 of the defeatable seal 106 disposed towards the diluent 103 and another surface 109 disposed towards the lyophilizate 104. The defeatable seal 106 further provides a sealing surface 110 that interfaces with interior sealing surface 111 of housing 100. The defeatable seal 106 is configured to maintain a sealed condition isolating the first compartment 101 from the second compartment 102 until the pressure within the first compartment 101 exceeds a specified design threshold whereupon the defeatable seal 106 fails and the first compartment 101 and second compartment 102 become in fluid communication with one another. Referring to FIG. 3A, the present disclosure further provides a hypodermic needle 112 permanently affixed to the housing 100 and resides in fluid communication with the second compartment 102. Referring to FIG. 3B, the present disclosure further discloses a removable needle shield 113 comprising an elastomer. Referring to FIG. 3C, a needle shield jacket 114 comprising a rigid material may optionally be provided. Referring to FIG. 3D, the needle shield 113 is geometrically configured to provide an enclosing sealing surface 115 about a portion of the exterior periphery 116 of the hypodermic needle 112 at its distal end and, concurrently, an interior sealing surface 117 about the exterior of an exterior sealing surface 118 disposed at the distal end of the housing 100. Upon installation of needle shield 113 in relationship with housing 100, the hypodermic needle 112, is isolated from the ambient environment until it is removed prior to use, as is the second compartment 102 and the lyophilizate 104 contained therein.

Figures 4A, 4B, 4C:
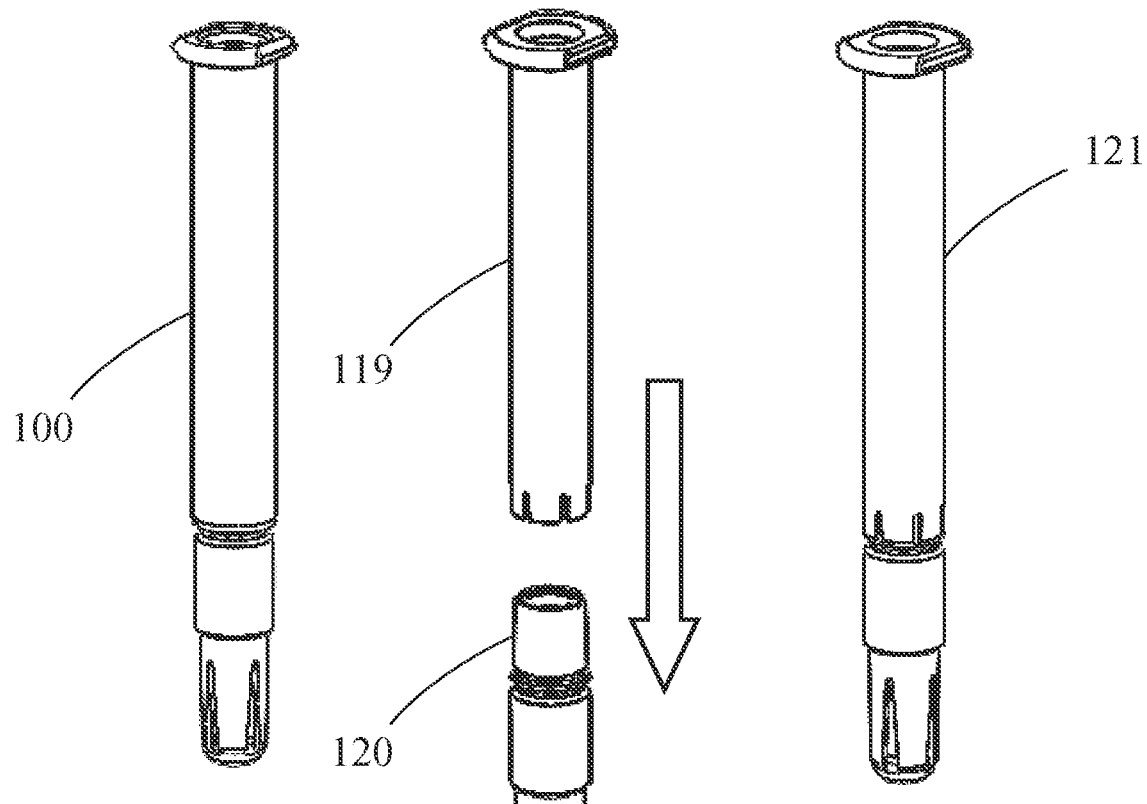
FIGS. 4A-4C illustrate first and second exemplary embodiments of the housing of the present disclosure.

Further, and referring to FIGS. 4A through 4C, the housing 100 may comprise a single, unitary member 100 as shown in FIG. 4A or a plurality of components, as shown in FIGS. 4B and 4C; diluent containment member 119 and lyophilizate containment member 120 being joined together to form alternative embodiment of housing 121 in accordance with a method to be described later in this disclosure.

Figure 5A:
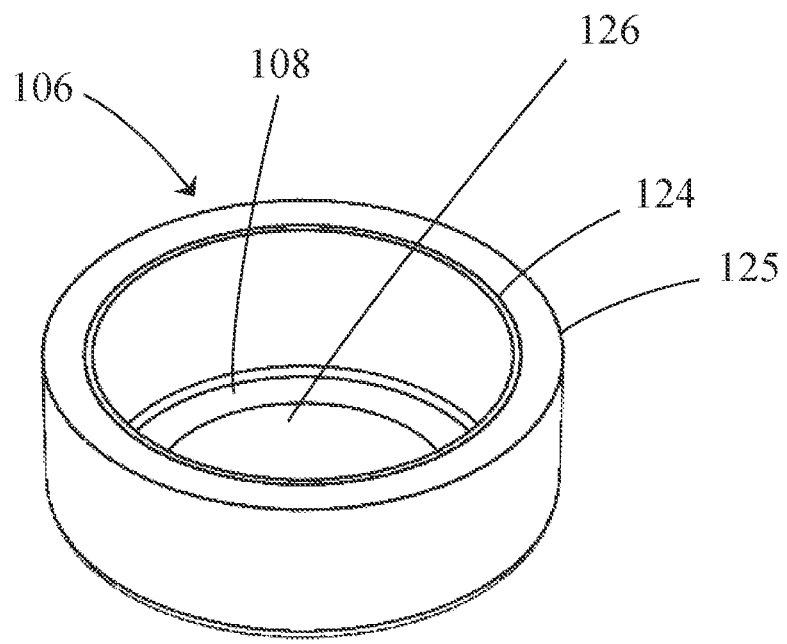
FIGS. 5A-5B illustrate an exemplary embodiment of the defeatable seal constituent of the present disclosure.
Figure 5B:
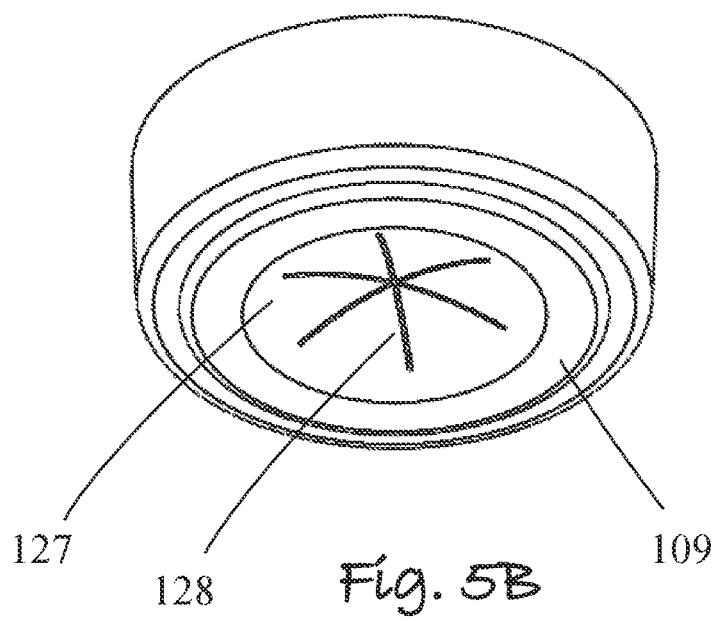

Referring to FIGS. 5A and 5B, an exemplary embodiment of the defeatable seal 106 is disclosed to illustrate one non-limiting embodiment. FIG. 5A illustrates the diluent-facing side 108 of the defeatable seal 106 while FIG. 5B illustrates the lyophilizate-facing side 109. The exemplary defeatable seal 106 disclosed is comprised of a semi-rigid rupture disk 124 and an elastomeric seal 125 disposed about the perimeter of the semi-rigid rupture disk 124. The elastomeric seal 125 may be formed upon the rupture disk 124 by, for example, insert molding, in a permanently bonded relationship. The rupture disk 124 comprises a proximally-directed convex surface 126 and a distally-directed concave surface 127. The rupture disk may further comprise one or more stress raiser groove 128 disposed about the distally-disposed concave surface 127. The stress raiser groove 128 is a feature that reduces the structural integrity of the rupture disk 124 at a particular location. Presence of the stress raiser groove 128 allows the rupture disk 124 to fail in a more predictable manner and with less pressure than a rupture disk lacking the stress raiser groove 128. Many other embodiments of a defeatable seal that can achieve the same utility are within the scope of the claims but are not presented here for the sake of brevity.

Figures 6A, 6B, 6C:
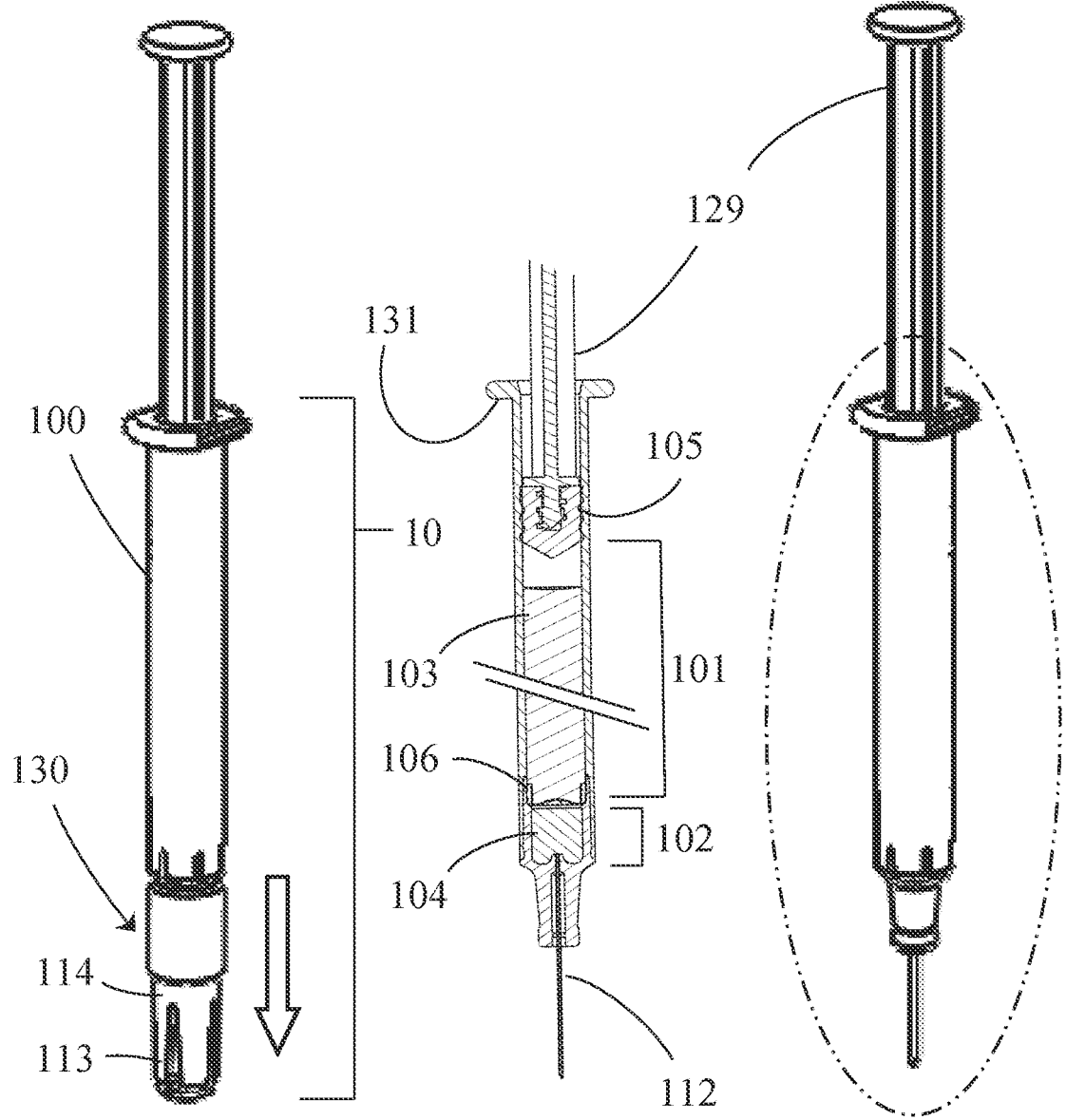
FIGS. 6A-6C illustrate a manually operable exemplary embodiment of the present disclosure.

Referring to FIGS. 6A and 6B, an exemplary embodiment of the present disclosure is described. A stem 129 is affixed to the piston 105 providing the means to manually operate the system 10. This exemplary embodiment of the system 10 includes a rigid needle shield 130 comprising a needle shield 113 assembled with a jacket 114. The system 10 is operable by first removing the rigid needle shield 130 from its engagement with the housing 100 thereby exposing the hypodermic needle 112. While grasping the housing 100 the hypodermic needle 112 is inserted into tissue at the injection site. Thereafter, while grasping the housing 100 in a manner allowing for a fingertip buttress to be provided upon the distally-disposed surface of the flange 131, an axial force is then applied to the stem 129 sufficient to initiate distally-directed movement of the piston 105 and thereby actuate the system 10. Considering the fact that the diluent 103 is an incompressible fluid, and, prior to failure of the defeatable seal 106 the first compartment is a closed volume; distally-directed movement of the piston 105 causes a rapidly increasing pressure within the first compartment 101. Once the increasing pressure exceeds the pressure that the defeatable seal 106 is designed to withstand, the defeatable seal 106 fails and fluid communication is established between the first compartment 101 and the second compartment 102. The diluent 103 begins to flow from the first compartment 101 past the now open defeatable seal 106 into the second compartment 102 and interacts with the lyophilizate 104 bringing the lyophilizate 104 into solution with the diluent 103. Upon continued force applied to the stem 129, the piston 105 progresses in the distal direction urging the diluent 103 out of the first compartment 101 and into the second compartment 102. The diluent 103 continues to accept the lyophilizate 104 into solution as flow proceeds through the second compartment 102, into and through the hypodermic needle 112, and into the tissue at the recipient's injection site. As diluent 103 continues to flow into and through the second compartment 102 taking lyophilizate 104 into solution, the concentration of drug per unit volume of injectate exiting the hypodermic needle 112 diminishes.

Referring to FIGS. 7A and 7B, other exemplary embodiments of the present disclosure is described. The embodiments shown on FIG. 7 are identical to that shown in FIG. 6 but without the stem 129. These embodiments are configured not to be manually operated as described in the previous paragraph but instead to become a constituent in a mechanized drug delivery system such as an auto-injector. In this application the function of the stem 129 is replaced by a stem-equivalent constituent of a mechanized drug delivery system driven by an internal powering means as described in the numerous hand-held automatic injection systems found in the prior art. These illustrative embodiments differ only in the presence or absence of the jacket 114; the system's response to the application of force upon the piston 105 is the same as that previously described.

A fraction of the medicament present in the lyophilizate 104 may remain within the second compartment 102 after all of the diluent 103 within the first compartment 101 is expelled. The amount of medicament remaining within the second compartment 102 is a function of the miscibility of the lyophilizate 104, the volumetric ratio of the second compartment 102 versus the first compartment 101, turbulence created within the second compartment 102 during fluid flow, among other potential factors. It is desirable that the maximum amount of medicament originally residing in the system 10 be injected into the recipient, as that remaining in the system 10 subsequent to the injection is wasted. Steps to accentuate the effectiveness of the system in order to minimize medicament residue are therefore desirable.

Figure 8A:
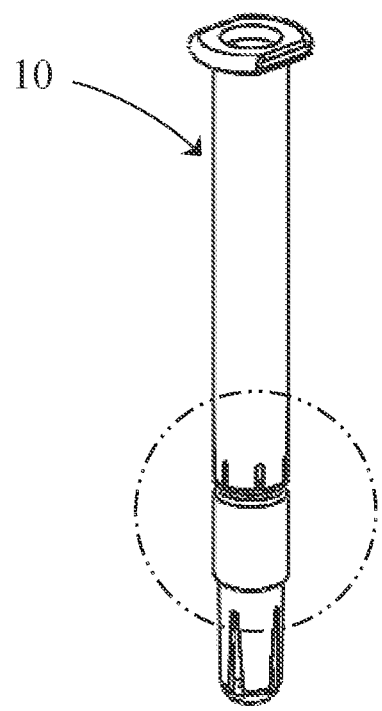
FIGS. 8A-8B provide a sectional view illustrating an exemplary embodiment of the present disclosure including a flow baffle and housing element intended to enhance mixing.
Figure 8B:
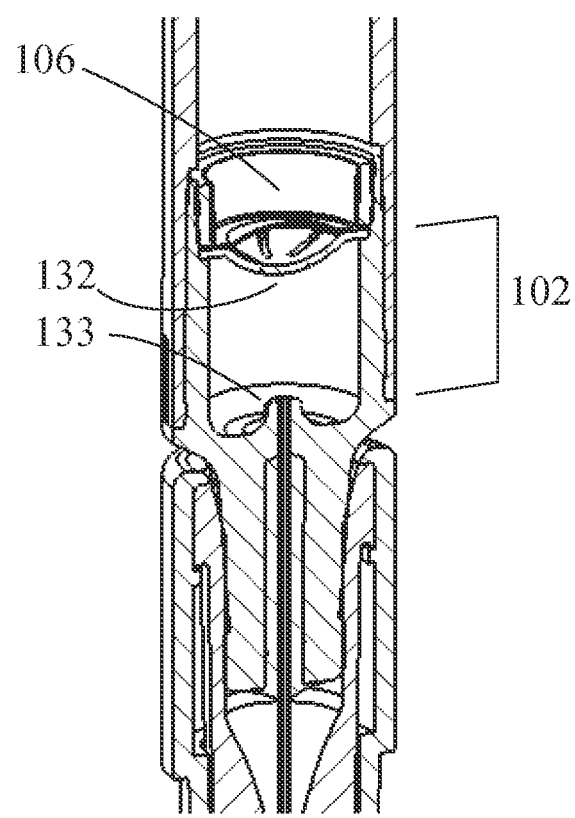

Referring to FIG. 8B, a cross-sectional view of the second compartment 102 describing an exemplary alternative embodiment of the system 10 (The diluent 103 and lyophilizate 104 are not shown for the purpose of clarity). A proximally-facing flow director 133 housing feature and a baffle 132 are disposed within the second compartment 102, with the baffle 132 being distal to the defeatable seal 106 and proximal to the lyophilizate 104. The flow director 133 and baffle 132 are presented to illustrate a non-limiting alternative embodiment of the system 10 intended to enhance turbulence within the second compartment 102 during diluent flow, encourage mixing of diluent 103 and lyophilizate 104, and boost the rate the lyophilizate 104 is mixed with the diluent 103.

Figures 9A, 9B:
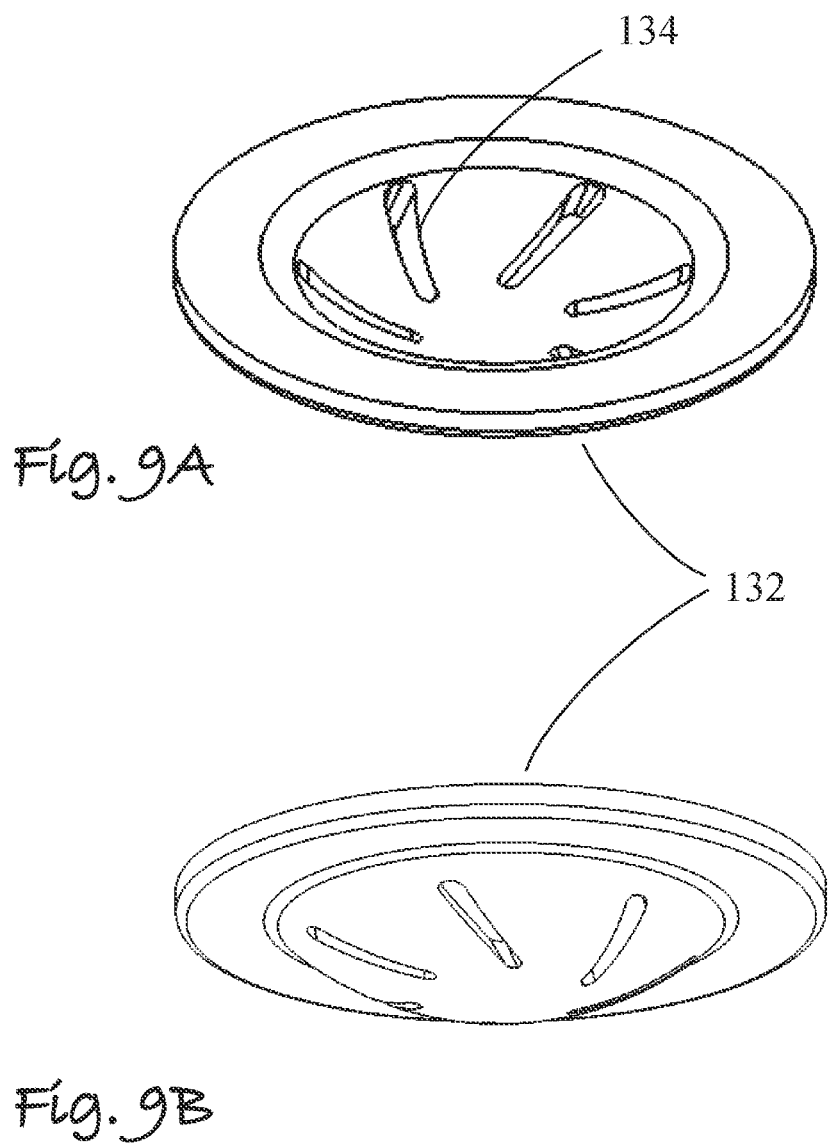
FIGS. 9A-9B provide details of a flow baffle element of an exemplary embodiment of the present invention.

Referring to FIG. 9, an exemplary embodiment of the baffle 132 is described. The baffle 132 is generally symmetric about its axis. A plurality of apertures 134 are disposed in a circular array about the baffle 132. Aperture 134 geometry is configured to accelerate and direct fluid flow in a semi-radial direction. Referring back to FIG. 8C, the exemplary embodiment of flow director 133 is configured in a proximally-disposed swept frustoconical shape urging distal flow of diluent 103 to be redirected into oncoming flow and reduce stagnation points within compartment 102.

Many other embodiments of elements of the present disclosure are possible within the scope of the claims but are not presented here for the sake of brevity.

Figures 10A, 10B, 10C, 10D:
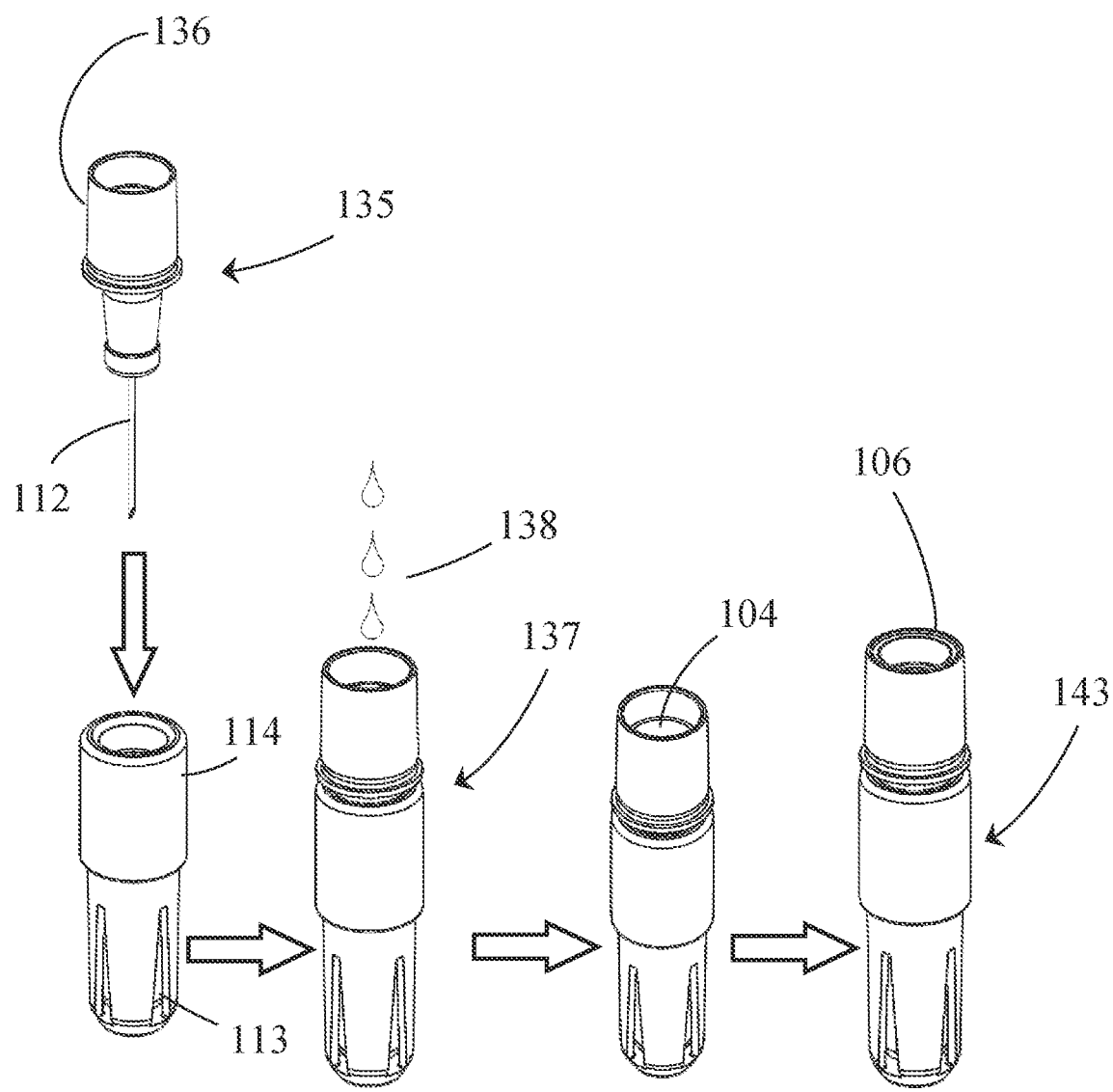
FIGS. 10A-10D illustrate a series of schematic diagrams depicting the production steps of an integrated injectable drug packaging and delivery system subassembly containing the lyophilized therapeutic substance.

There is disclosed further a plurality of methods of producing a ready-to-use system 10 containing a diluent 103 and lyophilizate 104. Referring to FIGS. 10A through 10D, a first exemplary embodiment and associated method describes the progression of pre-assembly of system 10 components, installation of the medicament solution to be lyophilized, lyophilization of the medicament, and installation of the defeatable seal 106. Referring to FIG. 10A, a lyophilizate compartment subassembly 135 comprises a lyophilizate compartment 136 and hypodermic needle 112 permanently joined together by, for example, epoxy bonding or insert molding. Lyophilizate compartment subassembly 135 is thereafter assembled with needle shield 113 and, optionally, needle shield jacket 114 to form a shielded lyophilizate compartment subassembly 137. Referring to FIG. 10B, the shielded lyophilizate compartment subassembly 137 is presented to a fill station and a unit dose of medicament solution 138 is dispensed into the open end of the shielded lyophilizate compartment subassembly 137. Referring to FIG. 10C, the shielded lyophilizate compartment subassembly 137 containing the medicament solution 138 is then exposed to the process conditions resulting in lyophilization of the medicament solution 138 and thus the formation of lyophilizate 104. Referring to FIG. 10D, upon completion of the lyophilization process the defeatable seal 106 is secured into the open end of the shielded lyophilizate compartment subassembly 137 to seal the lyophilizate 104 therein and thereby complete the lyophilizate-bearing system sub-assembly 143.

In some embodiments, the lyophilizate compartment subassembly 143 is configured to be compatible with industry-standard lyophilization processes and, once assembled with the subassembly of liquid containment member 119 as described later in this disclosure, is compatible with industry-standard pre-fillable syringe filling lines.

Referring to FIGS. 11A through F a second exemplary embodiment and associated method describes the progression of pre-assembly of system 10 components; installation of a removable fill tube, installation of the medicament solution to be lyophilized, lyophilization of the medicament, compaction of lyophilizate, removal of the compaction tool and fill tube and installation of the defeatable seal. Referring to FIGS. 11A, a removable fill tube 139 is temporarily assembled with the shielded lyophilizate compartment subassembly 137. Referring to FIG. 11B, this temporary assembly of fill tube 139 and shielded lyophilizate compartment subassembly 137 is then presented to a fill station and a unit dose of medicament solution 138 is dispensed into the open end of the shielded lyophilizate compartment subassembly 137 via the fill tube 139. In this embodiment and method, it is anticipated that the fill volume of the medicament solution 138 will exceed that of the lyophilizate compartment 136 and a portion of the medicament solution 138 will reside within the fill tube 139 after the filling process is completed. The temporary subassembly comprising the shielded lyophilizate compartment subassembly 137 and fill tube 139 collectively containing the medicament solution 138 is then exposed to the process conditions resulting in lyophilization of the medicament solution 138 and the formation of a higher volume lyophilizate 140. Referring to FIGS. 11C and 11D, the temporary subassembly comprising the shielded lyophilizate compartment subassembly 137 and fill tube 139 collectively containing the higher volume lyophilizate 140 is then presented to a tamping tool 141 dimensionally configured to cooperate in a close running fit with the interior bore of the fill tube 139. The tamping tool 141 is moved axially in the distal direction within the fill tube until the tamping tool 141 compacts the higher volume lyophilizate 140 into a volume compatible with the internal volume of the lyophilizate compartment 136. Referring to FIG. 11E, upon completion of the compaction step, the tamping tool 141 and fill tube 139 are withdrawn from engagement with the shielded lyophilizate compartment subassembly 137. Referring to FIG. 11F, upon removal of the tamping tool 141 and the fill tube 139 the defeatable seal 106 is installed into the open end of the shielded lyophilizate compartment subassembly 137 to seal the compacted lyophilizate 142 therein thereby completing the lyophilizate-bearing system subassembly 143.

Referring to FIGS. 12A through 12C, another exemplary embodiment and method is described wherein a baffle 132 is installed into the open end of the shielded lyophilizate compartment subassembly 137 and proximal to lyophilizate 104 (or compacted lyophilizate 142) prior to installation of the defeatable seal 106 to comprise the lyophilizate-bearing system sub-assembly with baffle 144.

Referring to FIG. 13A through 13D, an exemplary embodiment and associated method describes the progression of housing final assembly, installation of the diluent, and installation of the piston. Referring to FIG. 13A, a liquid containment member 119 and the lyophilizate-bearing system sub-assembly 143 (or optionally, the lyophilizate-bearing system sub-assembly with baffle 144) are brought into axial alignment. The liquid containment member 119 and the lyophilizate-bearing system sub-assembly are moved axially towards one another to engage snap fit features 145 disposed about the distal end of the liquid containment member 119 with a cooperating groove feature 146 disposed about the circumference of the lyophilizate containment member 120 constituent of the lyophilizate-bearing system sub-assembly 143. The liquid containment member 119 and lyophilizate-bearing system subassembly 143 (or optionally, the lyophilizate-bearing subassembly with baffle 144) are thereby secured to form a permanent and sealed system subassembly 147. Referring to FIG. 13B, the system subassembly 147 is thereafter presented to a fill station and diluent 103 is dispensed into the liquid containment member 119. Referring to FIG. 13C, the piston 105 is then introduced into the proximal end of the liquid containment member 119 and moved to its final position to complete system 10, as described in FIG. 13D.

Figure 14:
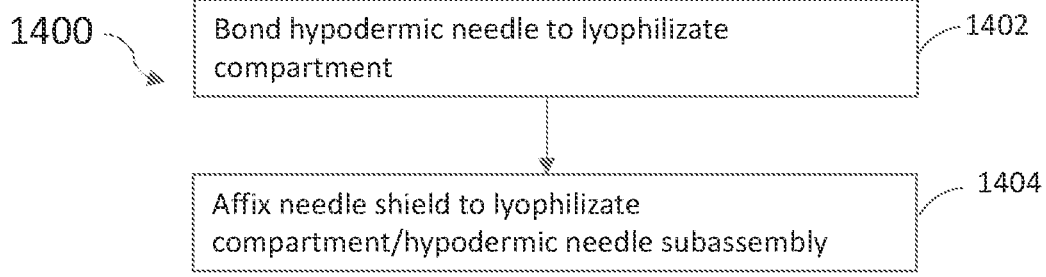
FIG. 14 illustrates a flowchart of a process for assembling a lyophilizate compartment subassembly in accordance with an illustrative embodiment.

FIG. 14 illustrates a flowchart of a process for assembling a lyophilizate compartment subassembly in accordance with an illustrative embodiment. Flowchart 1400 begins at Step 1402 by bonding a hypodermic needle to a lyophilizate compartment. In Step 1404 a needle shield is affixed to the lyophilizate compartment subassembly.

Figure 15:
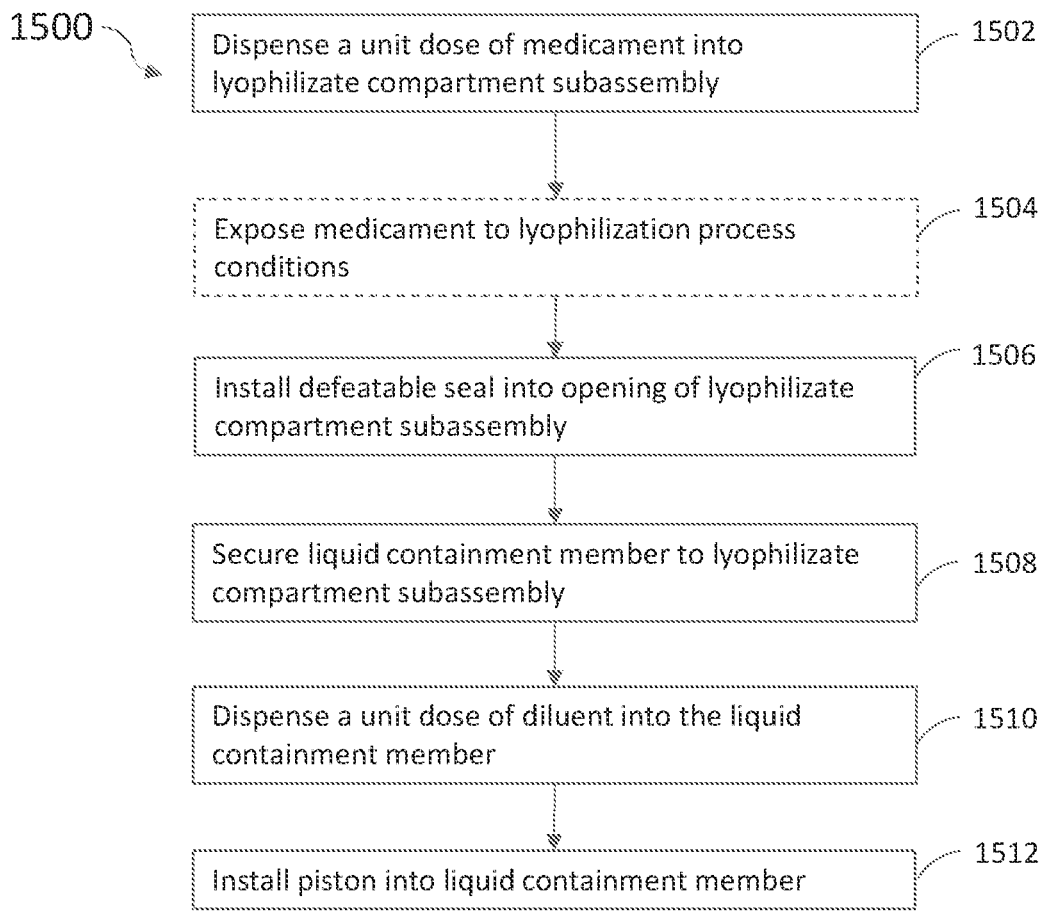
FIG. 15 illustrates a flowchart of a process for assembling an integrated injectable drug packaging and delivery system according to an illustrative embodiment.

FIG. 15 illustrates flowchart of a process for assembling an integrated injectable drug packaging and delivery system according to an illustrative embodiment. Flowchart 1500 begins at Step 1502 by dispensing a unit dose of a lyophilizate substance into an opening of a lyophilizate compartment subassembly. In some embodiments, the unit dose of the medicament exists in a liquid state. Accordingly, flowchart 1500 can include the optional Step 1504 of exposing the medicament solution to process conditions to form the lyophilizate. The process conditions can be a dehydration process that involves the manipulation of thermal energy and pressure to remove moisture.

In Step 1506, a defeatable seal is installed onto the opening of the lyophilizate compartment subassembly. In Step 1508 a liquid containment member is secured to the lyophilizate compartment subassembly. In Step 1510, a diluent is dispensed into the liquid containment member, and the liquid containment member is sealed with a slidable piston in Step 1512.

Figure 16:
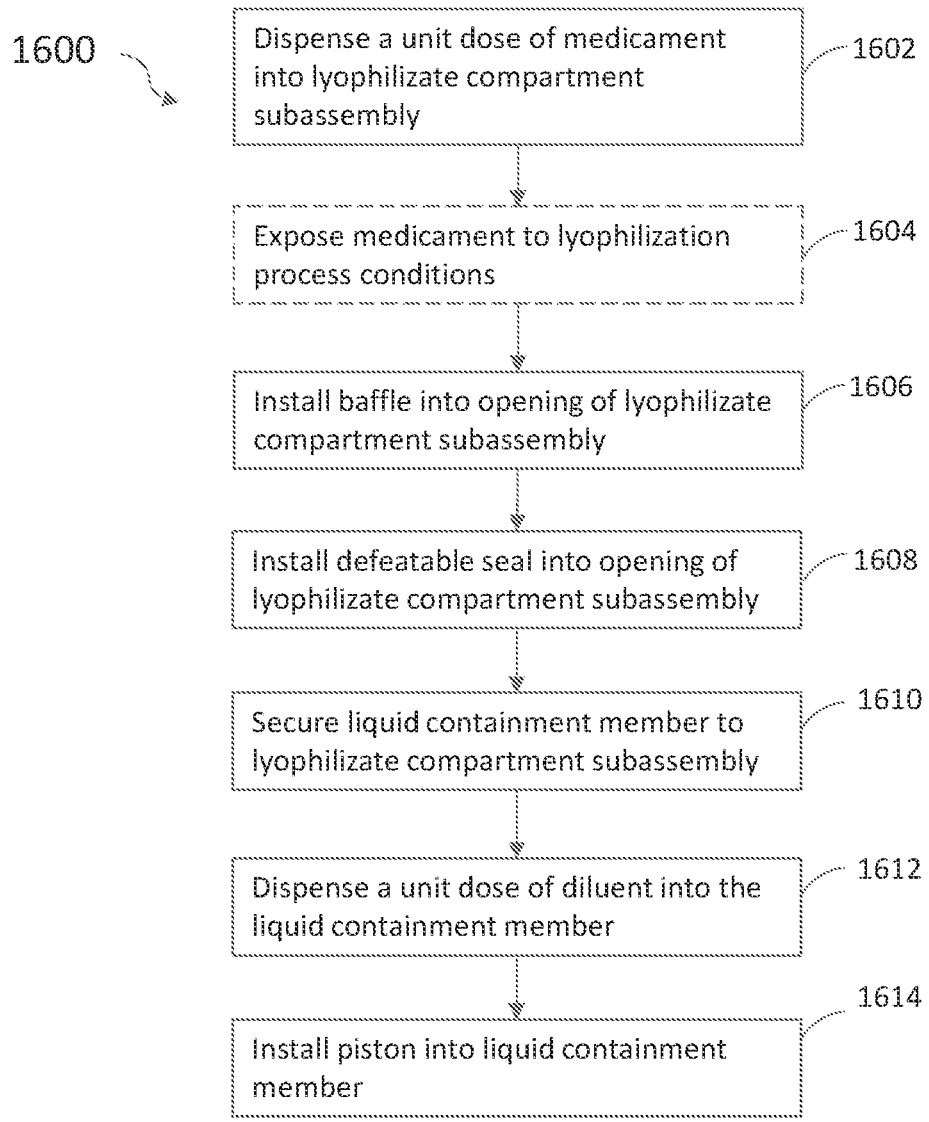
FIG. 16 illustrates a flowchart of a process for assembling an integrated injectable drug packaging and delivery system with a mixing baffle according to an illustrative embodiment.

FIG. 16 illustrates a flowchart of a process for assembling an integrated injectable drug packaging and delivery system with a mixing baffle according to an illustrative embodiment. Flowchart 1600 begins at Step 1602 by dispensing a unit dose of a lyophilizate substance into an opening of a lyophilizate compartment subassembly. In some embodiments, the unit dose of the medicament exists in a liquid state. Accordingly, flowchart 1600 can include the optional Step 1604 of exposing the medicament solution to process conditions to form the lyophilizate. The process conditions can be a dehydration process that involves the manipulation of thermal energy and pressure to remove moisture.

In Step 1606, a baffle is installed into the opening of the lyophilizate compartment subassembly, followed by installation of a defeatable seal onto the opening of the lyophilizate compartment subassembly in Step 1608. In Step 1610 a liquid containment member is secured to the lyophilizate compartment subassembly. In Step 1612, a diluent is dispensed into the liquid containment member, and the liquid containment member is sealed with a slidable piston in Step 1614.

Figure 17:
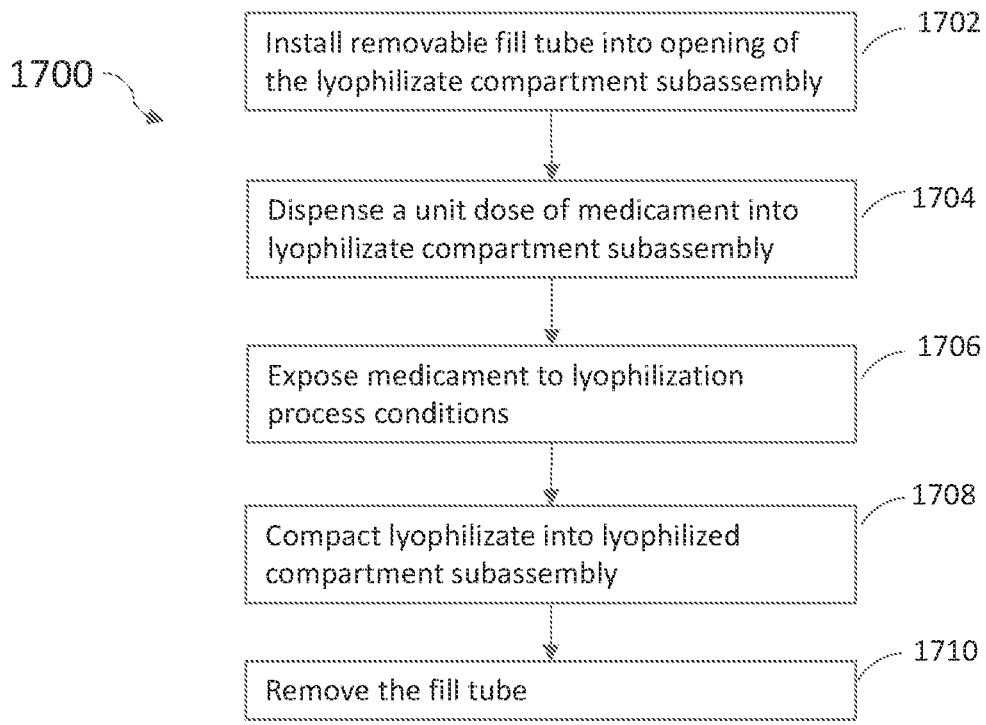
FIG. 17 illustrates a flowchart of a process for dispensing a unit dose of lyophilizate substance according to an illustrative embodiment.

FIG. 17 illustrates a flowchart of a process for dispensing the unit dose of lyophilizate compound according to an illustrative embodiment. Flowchart 1700 describes additional steps that may be necessary when the unit dose of lyophilizate is provided in solution, i.e., a medicament solution, with a volume that exceeds the volume of the second compartment configured for storing the lyophilizate substance.

Flowchart 1700 begins at Step 1702 by installing a removable fill tube at the opening of the lyophilizate compartment subassembly. In Step 1704, a medicament solution is dispensed into the open end of the lyophilizate compartment subassembly via the removable fill tube. The medicament solution at least partially fills a volume of the removable fill tube. In Step 1706, the medicament solution is exposed to process conditions to form the lyophilizate. In Step 1708, the lyophilizate is compacted into the lyophilized compartment subassembly, i.e., into the second compartment. Lastly, in Step 1710, the removable fill tube is removed. In one embodiment, the removable fill tube is removed by removably coupling a tamping tool with the removable fill tube during the compacting step. Here, the removable fill tube is withdrawn from the lyophilizate compartment subassembly by withdrawing the tamping tool and the removable fill tube away from the lyophilizate compartment subassembly.

Figure 18:
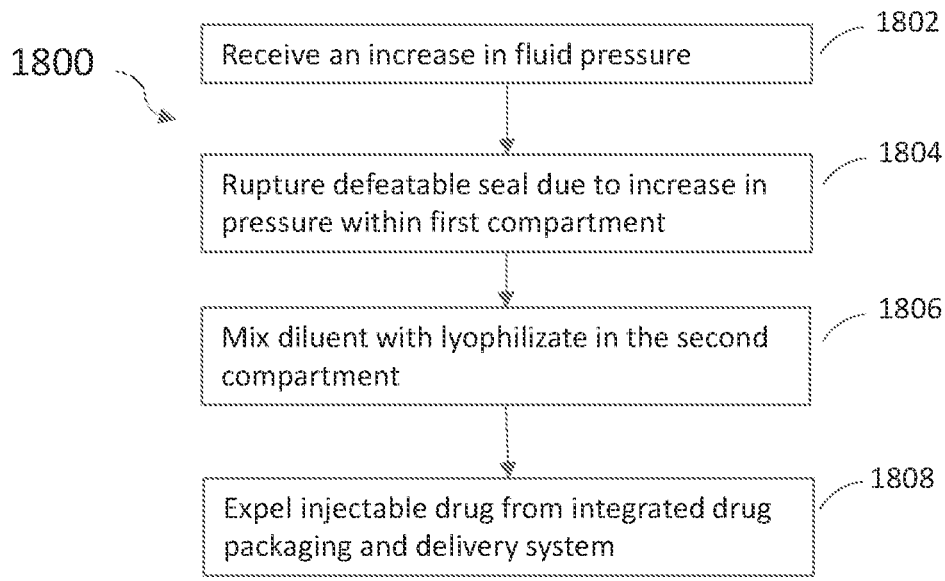
FIG. 18 is a flowchart of a process for using an integrated injectable drug packaging and delivery system according to an illustrative embodiment.

FIG. 18 is a flowchart of a process for using an injection apparatus according to an illustrative embodiment. The process can be carried out by an injection apparatus such as system 10 in FIG. 1 or the injection apparatus in FIG. 6. Flowchart 1800 begins at Step 1802 by receiving an increase in fluid pressure within the first compartment of the injection apparatus. In a non-limiting embodiment, the increase in the fluid pressure results from a compressive force applied to a piston that is slidably engaged within a housing of the injection apparatus. In one embodiment, the compressive force is provided by a stem that is coupled to the piston. In another embodiment, the compressive force is provided by a self-injection device. The compressive force causes an increase in fluid pressure within the first compartment.

In Step 1804, a defeatable seal separating the first compartment from the second compartment is ruptured by the increase in fluid pressure within the first compartment.

In Step 1806, a fluid sealed within the first compartment is mixed with a lyophilizate substance stored within the second compartment. The fluid can be any pharmaceutically-acceptable diluent suitable for in vivo applications. In a non-limiting embodiment, mixing is promoted by increasing turbulence of the fluid in the second compartment. Turbulence can be increased by passing the fluid through a baffle configured to accelerate velocity and impart rotational motion of the fluid as it enters the second compartment and then causing the fluid to flow against a flow director that redirects the fluid into the oncoming fluid flow. In Step 1808, the injectable drug formed from the mixture of diluent and lyophilizate substance is expelled from the injection apparatus. In one embodiment, the injectable drug is expelled from a hypodermic needle into a recipient's tissue.

Although embodiments of the disclosure have been described with reference to several elements, any element described in the embodiments described herein are exemplary and can be omitted, substituted, added, combined, or rearranged as applicable to form new embodiments. A skilled person, upon reading the present specification, would recognize that such additional embodiments are effectively disclosed herein. For example, where this disclosure describes characteristics, structure, size, shape, arrangement, or composition for an element or process for making or using an element or combination of elements, the characteristics, structure, size, shape, arrangement, or composition can also be incorporated into any other element or combination of elements, or process for making or using an element or combination of elements described herein to provide additional embodiments.

Additionally, where an embodiment is described herein as comprising some element or group of elements, additional embodiments can consist essentially of or consist of the element or group of elements. Also, although the open-ended term "comprises" is generally used herein, additional embodiments can be formed by substituting the terms "consisting essentially of" or "consisting of."

While this invention has been particularly shown and described with reference to preferred embodiments, it will be understood by those skilled in the art that various changes in form and detail may be made therein without departing from the spirit and scope of the invention. The inventor expects skilled artisans to employ such variations as appropriate, and the inventor intends the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

I claim:

1. An injection apparatus comprising:
    a housing with a proximate end and a distal end, wherein the housing defines a fluid pathway;
    a defeatable seal fixedly positioned within the fluid pathway against an abutment to separate an internal volume of the housing into a first compartment storing a fluid contacting the defeatable seal and sidewalls of the housing and a second compartment downstream from the first compartment; and
    a fluid outlet at the distal end of the housing,
    wherein the defeatable seal is configured to fail in response to an increase in fluid pressure within the first compartment, causing the fluid in the first compartment to pass through the second compartment and through the fluid outlet.

2. The injection apparatus of claim 1, wherein the housing is formed from a lyophilizate compartment subassembly coaxially aligned with a fluid containment member.

3. The injection apparatus of claim 1, wherein the defeatable seal further comprises:
    a rupture disk including a base; and
    an elastomeric seal circumscribing the rupture disk.

4. The injection apparatus of claim 3, wherein the base of the rupture disk further comprises at least one stress-raiser groove disposed on a distally-directed concave surface.

5. The injection apparatus of claim 1, further comprising:
    a baffle at an upstream end of the second compartment, wherein the baffle includes a plurality of apertures disposed in a circular array to increase fluid velocity and direct a flow of fluid in a semi-radial direction.

6. The injection apparatus of claim 5, further comprising:
    an end wall at a downstream end of the second compartment, wherein the end wall is a proximally-disposed, swept frustoconical shape configured to redirect the flow of fluid into oncoming fluid flow to promote mixing.

7. The injection apparatus of claim 1 further comprising:
    a hypodermic needle coupled to the distal end of the injection apparatus at the fluid outlet.

8. The injection apparatus of claim 1, further comprising:
    a piston slidable engaged within the first compartment, and wherein a compressive force applied to the piston causes the increase in fluid pressure within the first compartment.

9. An injection apparatus comprising:
    a housing with a proximate end and a distal end, wherein the housing defines a fluid pathway;
    a defeatable seal fixedly positioned within the fluid pathway against an abutment to separate an internal volume of the housing into a first compartment and a second compartment downstream from the first compartment;

a piston slidable engaged within the first compartment;

a diluent sealed in the first compartment between the piston and the defeatable seal, the diluent in contact with the defeatable seal and sidewalls of the housing;

a fluid outlet at the distal end of the housing;

a lyophilized substance sealed in the second compartment; and a hypodermic needle coupled to the fluid outlet, wherein the defeatable seal is configured to fail in response to an increase in fluid pressure caused by compressive force imparted to the piston, causing the diluent in the first compartment to mix with the lyophilized substance in the second compartment to form an injectate expelled from the hypodermic needle.

10. The injection apparatus of claim 9, wherein the defeatable seal further comprises:

a rupture disk including a base; and an elastomeric seal circumscribing the rupture disk.

11. The injection apparatus of claim 10, wherein the base of the rupture disk further comprises a proximally-directed convex surface.

12. The injection apparatus of claim 10, wherein the base of the rupture disk further comprises at least one stress-raiser groove disposed on a distally-directed concave surface.

13. The injection apparatus of claim 9, further comprising:

a baffle at an upstream end of the second compartment, wherein the baffle includes a plurality of apertures disposed in a circular array to increase fluid velocity and direct a flow of fluid in a semi-radial direction.

14. The injection apparatus of claim 13, further comprising:

an end wall at a downstream end of the second compartment, wherein the end wall is a proximally-disposed, swept frustoconical shape configured to redirect the flow of fluid into oncoming fluid flow to promote mixing.

15. The injection apparatus of claim 9, wherein the housing is formed from a lyophilizate compartment subassembly coaxially aligned with a fluid containment member and permanently secured thereto.

16. A method for operating an injection apparatus that includes a housing with proximate end and a distal end, and a defeatable seal fixedly positioned against an abutment within a fluid pathway defined by the housing, wherein the defeatable seal separates an internal volume of the housing into a first compartment and a second compartment downstream from the first compartment, the method comprising:

receiving an increase in fluid pressure within the first compartment, the increase in the fluid pressure exerted against a fluid contacting the defeating seal and sidewalls of the housing; and rupturing the defeatable seal from the increase in the fluid pressure within the first compartment; and passing the fluid in the first compartment through the second compartment and through a fluid outlet at a distal end of the housing from the increase in the fluid pressure within the first compartment.

17. The method of claim 16, wherein the injection apparatus includes a piston slidably engaged within the first compartment, and wherein the method further comprises:

receiving a compressive force applied to the piston to cause the increase in the fluid pressure in the first compartment.

18. The method of claim 16, wherein the second compartment houses a lyophilized substance, and wherein passing the fluid in the first compartment through the second compartment further comprises:

mixing the fluid and the lyophilized substance.

19. The method of claim 18, wherein a hypodermic needle is coupled to the fluid outlet, and wherein the method further comprises:

expelling the fluid and the lyophilized substance from the hypodermic needle.

* * * * *